United States Patent [19]

Prather

[11] Patent Number: 5,268,736
[45] Date of Patent: Dec. 7, 1993

[54] LIGHT ABSORPTION CELL COMBINING VARIABLE PATH AND LENGTH PUMP

[76] Inventor: William S. Prather, 2419 Dickey Rd., Augusta, Ga. 30906

[21] Appl. No.: 843,334

[22] Filed: Feb. 28, 1992

[51] Int. Cl.⁵ .................. G01N 21/05; G01N 21/85
[52] U.S. Cl. .................... 356/246; 250/576; 356/440
[58] Field of Search ............ 356/246, 436, 440, 409, 356/410; 250/576

[56] References Cited

U.S. PATENT DOCUMENTS

| | | | |
|---|---|---|---|
| 3,142,719 | 7/1964 | Farr | 88/14 |
| 3,448,277 | 6/1969 | Jayko | 250/218 |
| 3,740,156 | 6/1973 | Heigl et al. | 356/204 |
| 3,810,695 | 5/1974 | Shea | 356/246 |
| 3,843,269 | 10/1974 | Hohberg | 356/205 |
| 4,019,372 | 4/1977 | Parkell et al. | 356/410 |
| 4,111,560 | 9/1978 | Jolanki et al. | 356/410 |
| 4,451,152 | 5/1984 | Topol et al. | 356/440 |
| 4,488,814 | 12/1984 | Johnson | 356/414 |
| 4,786,171 | 11/1988 | LeFebre et al. | 356/436 |
| 4,950,610 | 8/1990 | Tittle | 356/435 |
| 5,039,224 | 8/1991 | O'Rourke et al. | 356/440 |
| 5,146,294 | 9/1992 | Grisar et al. | 356/246 |

*Primary Examiner*—Richard A. Rosenberger
*Attorney, Agent, or Firm*—Brian R. Tumm; Harold M. Dixon; William R. Moser

[57] ABSTRACT

A device for use in making spectrophotometric measurements of fluid samples. In particular, the device is a measurement cell containing a movable and a fixed lens with a sample of the fluid therebetween and through which light shines. The cell is connected to a source of light and a spectrophotometer via optic fibers. Movement of the lens varies the path length and also pumps the fluid into and out of the cell. Unidirectional inlet and exit valves cooperate with the movable lens to assure a one-way flow of fluid through the cell. A linear stepper motor controls the movement of the lens and cycles it from a first position closer to the fixed lens and a second position farther from the fixed lens, preferably at least 10 times per minute for a nearly continuous stream of absorption spectrum data.

12 Claims, 1 Drawing Sheet

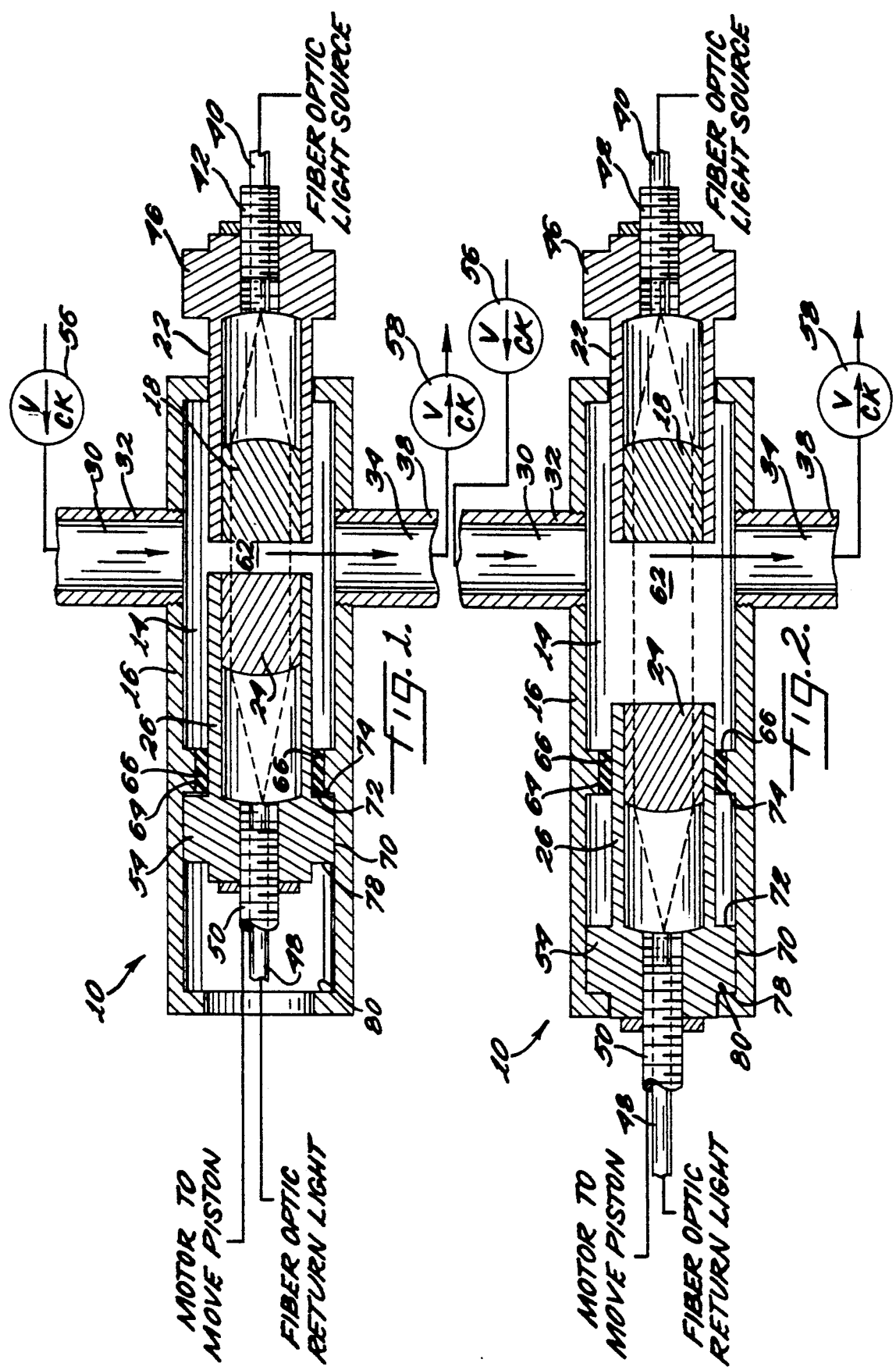

LIGHT ABSORPTION CELL COMBINING VARIABLE PATH AND LENGTH PUMP

The U.S. Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to devices for measuring characteristic absorption of fluid samples or gas samples. More particularly, the present invention relates to a spectrophotometric measurement cell that also pumps fluid samples into and out of the cell.

2. Discussion of Background

Light absorption cells that measure the characteristic absorption spectrum in a fluid sample are well known in the prior art. A typical spectrophotometer measurement system includes a light source, a sample cell, and a detector. The sample cell usually contains a lens to direct the light from the light source through the sample fluid, and a second lens to direct light coming from the sample fluid to the detector. The absorption spectrum from the light passing through the sample cell is measured by the detector. Often, spectrophotometric measurements are taken from a known or reference sample, such as distilled water, and then compared to measurements taken from the fluid sample. Comparison with the known or reference sample assists in the determination of the concentraions of various components in the fluid sample.

Several spectrophotometric measuring devices have fixed distances between the light source and the detector. For instance, Topol et al., U.S. Pat. No. 4,451,152, and Farr, U.S. Pat. No. 3,142,719, disclose measuring chambers with a light source and a detector on opposing sides of the chamber, a fixed distance apart. The fluid sample is drawn into the chamber by a piston, and the intensity of the light transmitted through the sample is measured.

It is often desirable to have the measurement capability of varying the optical path length. Johnson, U.S. Pat. No. 4,488,814, and Jayko U.S. Pat. No. 3,448,277, disclose devices that vary the optical path length by changing the distance between the light source and the detector. Jayko uses a syringe tube configuration to enable a plunger to vary the optical path length between the light source and the detector. The syringe tube also draws the fluid sample into the measuring environment between the light source and the detector. However, neither of these devices appears to be suitable for on-line use.

Heigl, et al., U.S. Pat. No. 3,740,156, discloses a photometric sampling cell device for on-line analysis of process streams. The sample cell, which is positioned within the process stream, contains two windows, one of which can be manually adjusted a predetermined distance from the other window while in the process stream. The fluid sample is located within the sample cell between the two windows. Measurement can then be made as light from a conventional source passes through one of the windows, through the sample, then through the other window to a receiver. However, the adjustment of the windows is manual and cannot readily be done while measurements are in progress.

A probe for making remote optical absorption measurements is disclosed by O'Rourke, et al., U.S. Pat. No. 5,039,224. The probe allows variable optical path length by using a sliding, reflecting plug to reflect light coming from the light source through the fluid sample and back to a detector. The mechanical movement of the sliding plug allows the optical path length to be varied remotely and while spectral measurements are in progress. The probe has ports for admitting and expelling the fluid sample.

Despite the existence of numerous spectrophotometric measuring devices, it is believed that no device uses a portion of the measurement means to vary the optical path length and also to pump the fluid sample into and out of the measurement cell, thereby eliminating the need for a separate means for feeding the fluid sample to and from the measurement cell. It would also be desirable for such a device to be able to mechanically vary the optical path length during the process of making spectral measurements, thus allowing the measurement cell to be used on-line.

SUMMARY OF THE INVENTION

According to its major aspects and broadly stated, the present invention is a device for making spectrophotometric measurements of fluid samples. In particular, it comprises a measurement cell with an inlet and an exit valve and a movable and a fixed lens. Moving the movable lens both varies the path length between the movable lens and the fixed lens and also pumps the sample of fluid into and out of the cell. The measurement cell is connected to a light source and a spectrophotometer by optic fibers. The movable lens is mechanically controlled by a stepper motor that allows the movable lens to move linearly and rapidly toward and away from the fixed lens. The use of one-way entry and exit valves to maintain a unidirectional fluid sample flow cooperates with the movement of the movable lens to pump the fluid. Light from the light source enters the cell, passes through the fluid sample interposed in the space between the fixed lens and the movable lens, and exits the cell to the detector or measuring device. To reference the sample measurement, the movable lens is linearly moved toward the fixed lens, thereby expelling most of the fluid sample between the two lenses so that, when light is transmitted, it passes through very little of the fluid sample. To make a sample measurement, the movable lens is moved a desired distance away from the fixed lens, thereby causing a fluid sample to be drawn between the two lenses. Thus, the transmitted light passes through the fluid sample and thence to a spectrophotometer for analysis. The movable lens can be operated continuously, pumping sample fluid out of the cell while drawing new sample fluid into the cell as spectral measurements are being made, thus allowing continuous sampling sequences.

An important feature of the present invention is dual function of the movable lens. The optical path length can be varied and the fluid can be pumped into and out of the cell by movement of the lens. There are then fewer moving parts and simplified manufacturing.

Another feature of the present invention is the use of one-way entry and exit valves at the sides of the measurement cell. With this feature, a fluid sample in the cell can only be expelled through an exit port controlled by the exit valve, and any new fluid sample can only be admitted through an entry port controlled by the entry valve. Thus, the one-way valves assure a unidirectional flow of fluid sample through the measurement area of the cell. The unidirectional flow cooperates with and enables the cell's movable lens to function as a fluid sample pump in addition to its use in making spectral measurements of fluid samples and prevents a previous sample from re-entering the cell for a second measurement.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a side, cross sectional view of a cell in the reference position according to a preferred embodiment of the present invention; and FIG. 2 is a side, cross sectional view of the cell of FIG. 1 in the sample measuring position.

DETAILED DESCRIPTION OF A PREFERRED EMBODIMENT

Referring now to FIGS. 1 and 2, measuring device 10 comprises a measurement cell body 16 defining a measurement cell interior 14, a fixed lens 18 contained within a fixed lens assembly 22, a movable lens 24 contained within a linearly movable lens assembly 26, an inlet 30 defined by an inlet port 32 and an exit 34 defined by an exit port 38 in the sides of cell body 16. Fluid sample enters cell interior 14 through inlet 30 and exits cell interior 14 through exit 34.

A fiber optic source cable 40 in optical communication with a light source (not shown) is contained within a housing 42 and connected to fixed lens assembly 22 through a fitting 46. Similarly, a fiber optic return cable 48 in optical communication with an optical detector (not shown) and contained within a housing 50 is connected to movable lens assembly 26 through a fitting 54. Additionally, movable lens assembly 26 is connected to and mechanically controlled by a motor (not shown), preferably a stepper motor, that allows movable lens assembly 26 to move movable lens 24 linearly within measurement cell interior 14.

A one-way entry valve 56 is positioned in series with inlet 30 to assist in controlling the flow of new fluid sample into measurement cell interior 14. Also, a one-way exit valve 58 is positioned in series with outlet 34 to assist in controlling the flow of current fluid sample out of measurement cell interior 14.

Movable lens 24 is positioned within measurement cell interior 14 and axially aligned to fixed lens 18, which is also positioned within cell interior 14. Thus, a fluid sample measuring volume 62 is defined between movable lens 24 and fixed lens 18. Because of the linear movement capability of movable lens 24, measuring volume 62 can vary in size. Movable lens 24 can be a first or reference distance away from fixed lens 18 (as in FIG. 1) and a first or reference spectrophotometric measurement can be made. Subsequently, movable lens 24 can be moved linearly a second distance from fixed lens 18 (as in FIG. 2) and a spectrophotometric measurement representative of the fluid sample contained within measurement cell interior 14 can be made.

In addition to varying the distance between lenses and allowing various sample measurements to be made, the linear movement of lens assembly 26 allows movable lens 24 to function as a pump when used in conjunction with the unidirectional flow of fluid sample caused by entry valve 56 and exit valve 58. When moving toward fixed lens 18, movable lens 24 forces the fluid sample from measurement cell interior 14 and out of measurement cell interior 14 through exit 34 and exit valve 58. Conversely, linear movement of movable lens 24 away from fixed lens 18 draws new sample fluid into measurement cell interior 14 through inlet valve 56 and inlet 30. An opening 64 defined by an airtight seal 66 allows movable lens assembly 26 to move linearly into and out of measurement cell interior 14. Seal 66 assures that measurement cell interior 14 remains airtight, thus allowing the movement of movable lens 24 away from fixed lens 18 to create a vacuum which will draw new fluid sample into measurement cell interior 14.

In use, a motor (not shown) attached to movable lens assembly 26 positions movable lens 24 a first distance away from fixed lens 18 so that very little sample fluid is between fixed lens 18 and movable lens 24 (as in FIG. 1). This first distance is minimized by the particular configuration of fitting 54. Fitting 54 has an annular extension 70 having a first face 72 which comes in contact with an indented portion 74 of cell body 16 to prevent further movement of lens assembly 26 and movable lens 24 toward fixed lens 18. Extension 70 of fitting 54 can be altered to vary the least possible distance between movable lens 24 and fixed lens 18. Once movable lens 24 is a first distance away from fixed lens 18, a reference measurement is taken by carrying light from a light source (not shown) through optic cable 40 to fixed lens assembly 22. The light then travels through fixed lens 18, through measurement area 62 containing fluid sample, and through movable lens 24. From movable lens 24, the light travels through optic cable 48 to an optical detector (not shown) for analysis.

Movable lens 24 is then moved a second distance away from fixed lens 18 so that a sample measurement can be made (as in FIG. 2). The distance between movable lens 24 and fixed lens 18 is maximized when a second face 78 of annular extension 70 comes in contact with an end face 80 of cell body 16. End face 80 has a hole dimensioned to receive a portion of fitting 54, housing 50, and optic cable 48 when movable lens assembly 26 is positioned to maximize the distance between movable lens 24 and fixed lens 18. Once movable lens 24 is a desired distance away from fixed lens 18, a sample measurement can be made. Light from a light source (not shown) is carried through optic cable 40 to fixed lens 18. The light then travels through measurement area 62, which contains fluid sample. The light then travels through movable lens 24 to optic cable 48 and to a spectrophotometric detector for analysis.

The motorized movable lens assembly 26 can then move movable lens 24 toward and away from fixed lens 18 in a series of rapid or deliberate cycles preferably at least 10 cycles per second. Each movement of movable lens 24 toward fixed lens 18 expels fluid sample currently contained in measurement cell interior 14 out of measurement cell interior 14 through exit 34 and outlet valve 58. Each movement of movable lens 24 away from fixed lens 18 draws new fluid sample into measurement cell interior 14 through inlet valve 56 and inlet 30. The number of linear movement cycles of the movable lens 24 will determine how much of the fluid sample in measurement cell interior 14 is expelled and subsequently how much new fluid sample is drawn into measurement cell interior 14. The higher the number of cycles, the more measurements that can be taken and the closer the absorption spectrum data approaches continuous measurement and real time analysis of sample concentration.

It will be apparent to those skilled in the art that many changes and substitutions can be made to the preferred embodiment herein described without departing from the spirit and scope of the present invention as defined by the appended claims.

What is claimed is:

1. Apparatus for use with a source of light and a spectrophotometer, said apparatus for making spectrophotometric measurements of a fluid sample, said apparatus comprising:
   a cell having an interior;
   valve means for controlling access of said fluid sample into and out of said interior of said cell;
   pumping means for moving said fluid sample into and out of said cell interior;
   a fixed lens in said interior; and
   a movable lens in said interior and spaced apart from said fixed lens so that said fluid sample may move into the space therebetween, said pumping means moving said movable lens toward and away from said fixed lens, movement of said movable lens causing said fluid to be pumped into and out of said cell interior.

2. The apparatus as recited in claim 1, wherein said pumping means moves said movable lens repeatedly between a first distance from said fixed lens and a second distance from said fixed lens.

3. The apparatus as recited in claim 1, wherein said pumping means moves said movable lens between a first distance from said fixed lens and a second distance from said fixed lens at least ten cycles per minute.

4. The apparatus as recited in claim 1, wherein said pumping means further comprises a stepper motor attached to said movable lens and adapted to move said movable lens toward and away from said fixed lens between a first position and a second position at least ten cycles per minute, each of said cycles occurring when said movable lens moves from said first position to said second position and then back to said first position.

5. The apparatus as recited in claim 1, wherein said valve means further comprises an entry valve and an exit valve, said entry valve only allowing the admission of sample fluid into said cell interior, said exit valve only allowing the expulsion of said sample fluid from said cell interior.

6. The apparatus as recited in claim 1, wherein said apparatus further comprises an optical means for carrying light to and from said apparatus.

7. Apparatus for use with a source of light and a spectrophotometer for making spectrophotometric measurements of a fluid sample, said apparatus comprising:
   a measurement cell having an interior;
   a fixed lens positioned within said measurement cell interior;
   a movable lens slidably positioned in said measurement cell interior, said movable lens axially aligned to and spaced apart from said fixed lens and defining a measuring area therebetween;
   means for linearly moving said movable lens between a reference position a first distance with respect to said fixed lens and a sampling position a second distance from said fixed lens, said linear movement means causing said movable lens to pump said fluid sample out of said measuring area and causing a new fluid sample to be drawn into said measuring area; and
   valve means for allowing the admission of said fluid sample into and the expulsion of said fluid sample out of said measurement cell interior in response to movement of said movable lens by said moving means.

8. The apparatus as recited in claim 7, wherein said moving means is a stepper motor, said stepper motor moving said movable lens back and forth between said reference position and said sampling position at least approximately ten times per minute.

9. The apparatus as recited in claim 7, wherein said apparatus further comprises an optical means for carrying light to and from said measuring area of said apparatus.

10. The apparatus as recited in claim 7, wherein said valve means further comprises an entry valve and an exit valve, said entry valve only allowing the admission of sample fluid into said cell interior, said exit valve only allowing the expulsion of said sample fluid from said cell interior.

11. A method for making spectrophotometric measurements of a fluid sample, said method using a measurement cell having an interior containing a fixed lens and a movable lens, said movable lens slidably positioned within the interior of said measurement cell and spaced apart from said fixed lens and defining a space therebetween, and an inlet valve and an exit valve, said method comprising the steps of:
   opening said exit valve;
   closing said inlet valve;
   moving said movable lens toward said fixed lens, thereby causing said movable lens to pump any existing fluid sample from said measurement cell interior through said exit valve and reducing the space therebetween;
   directing a source of light through said space between said movable lens and said fixed lens via said movable lens and said fixed lens whereby a spectrum of light absorption can be obtained;
   closing said exit valve;
   opening said inlet valve;
   moving said movable lens apart from said fixed lens so that a new sample of said fluid is pumped into said space therebetween; and
   directing a source of light through said new sample using said movable lens and said fixed lens whereby a spectrum of light absorption of said sample can be obtained.

12. The method as recited in claim 11, wherein said movable lens is moved toward and away from said fixed lens at least approximately ten times per minute.

* * * * *